US006783559B2

(12) United States Patent
De La Mettrie et al.

(10) Patent No.: US 6,783,559 B2
(45) Date of Patent: Aug. 31, 2004

(54) COMPOSITION FOR THE OXIDATION DYEING OF KERATIN FIBRES AND DYEING PROCESS USING THIS COMPOSITION

(75) Inventors: Roland De La Mettrie, Le Vesinet (FR); Jean Cotteret, Verneuil-sur-Seine (FR); Arnaud De Labbey, Aulnay Sous Bois (FR); Mireille Maubru, Chatou (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/319,204
(22) PCT Filed: Sep. 28, 1998
(86) PCT No.: PCT/FR98/02074
§ 371 (c)(1),
(2), (4) Date: Jun. 30, 1999
(87) PCT Pub. No.: WO99/17729
PCT Pub. Date: Apr. 15, 1999

(65) Prior Publication Data
US 2003/0009833 A9 Jan. 16, 2003

(30) Foreign Application Priority Data
Oct. 3, 1997 (FR) .......................... 97 12351

(51) Int. Cl.$^7$ ................................ A61K 7/13
(52) U.S. Cl. .................. 8/407; 8/408; 8/409; 8/410; 8/411; 8/424
(58) Field of Search ................ 8/401, 407–411, 8/424

(56) References Cited

U.S. PATENT DOCUMENTS

| | | | |
|---|---|---|---|
| 3,884,627 A | * | 5/1975 | Brody et al. |
| 3,907,799 A | | 9/1975 | O'Brien et al. ............ 544/281 |
| 4,065,255 A | * | 12/1977 | Andrillon et al. ............ 8/412 |
| 4,277,244 A | * | 7/1981 | Bugaut et al. ............ 8/410 |
| 4,840,639 A | * | 6/1989 | Husemeyer et al. ............ 8/412 |
| 4,961,925 A | | 10/1990 | Tsujino et al. ............ 8/401 |
| 5,514,188 A | * | 5/1996 | Cotteret et al. ............ 8/412 |
| 5,567,421 A | * | 10/1996 | Cotteret et al. ............ 8/408 |
| 5,833,969 A | * | 11/1998 | Tsujino et al. ......... 424/70.122 |
| 5,849,041 A | * | 12/1998 | Kunz et al. ............ 8/408 |
| 6,027,719 A | * | 2/2000 | Tomura et al. .......... 424/78.02 |
| 6,241,784 B1 | * | 6/2001 | De La Mettrie et al. |
| 6,342,078 B1 | * | 1/2002 | De La Mettrie et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| DE | 195 47 991 | 6/1997 |
| EP | 0 310 675 | 4/1989 |
| EP | 0 628 559 | 12/1994 |
| EP | 0 716 846 | 6/1996 |
| EP | 0 766 958 | 4/1997 |
| EP | 0 795 313 | 9/1997 |
| FR | 2 586 913 | 3/1987 |
| FR | 2 733 749 | 11/1996 |
| GB | 1 026 978 | 4/1966 |
| GB | 1 153 196 | 5/1969 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO 97/24105 | 7/1997 |
| WO | 98/22078 | * 5/1998 |

OTHER PUBLICATIONS

Vishnu J. Ram et al., "Synthesis of bioisosteric pyrazolo[1, 5–a]pyrimidines as leishmanicides", Indian Journal of Chemistry, vol. 34B, Jun. 1995, pp. 514–520.

Nadia S. Ibraham et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Robert H. Springer et al., "Synthesis and Enzymic Activity of 6–Carbethoxy– and 6–Ethoxy–3,7–disubstituted–pyrazolo[1,5–α]pyrimidines and Related Derivatives as Adenosine Cyclic 3',5'–Phosphate Phosphodiesterase Inhibitors", Journal of Medicinal Chemistry, vol. 25, No. 3, 1982, pp. 235–242, no month available.

Thomas Novinson et al., "Synthesis and Antifungal Properties of Certain 7–Alkylaminopyrazolo[1,5–a]pyrimidines", Journal of Medicinal Chemistry, vol. 20, No. 2, 1977, pp. 296–299, no month available.

Alexander McKillop et al., "Reaction of Hydrazine with β–Aminocrotononitrile: Synthesis of 2,7–dimethyl– 5–aminopyrazolo[1,5–a]pyrimidine", Heterocycles, vol. 6, Nos. 9, 10, 1977, pp. 1355–1360, no month available.

Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480, no month available.

Ermitas Alcade et al., "Etude de la réaction du β–aminocrotonitrile et du α–formyl phénylacétonitrile avec l'hydrazine: synthèse d'amino-7 pyrazolo[1,5–a]pyrimidines", Journal of Heterocyclic Chemistry, vol. 11, No. 3, Jun. 1974, pp. 423–429.

(List continued on next page.)

*Primary Examiner*—Margaret Einsmann
(74) *Attorney, Agent, or Firm*—Finnegan, Henderson, Farabow, Garrett & Dunner, L.L.P.

(57) ABSTRACT

The invention relates to a ready-to-use composition for the oxidation dyeing of keratin fibres, and in particular human keratin fibres such as the hair, comprising, in a medium which is suitable for dyeing, at least one first oxidation base chosen from para-phenylenediamine derivatives, double bases, ortho-aminophenols and heterocyclic bases, at least one second oxidation base chosen from para-aminophenols, at least one meta-aminophenol as coupler and at least one enzyme of 2-electron oxidoreductase type in the presence of at least one donor for the said enzyme, and to the dyeing process using this composition.

23 Claims, No Drawings

OTHER PUBLICATIONS

English language Derwent Abstract of DE 23 59 399, Jun. 1975.
English language Derwent Abstract of DE 38 43 892, Jun. 1990.
English language Derwent Abstract of DE 41 33 957, Apr. 1993.
English language Derwent Abstract of DE 195 43 988, May 1997.
English language Derwent Abstract DE 195 47 991, Jun. 1997.
English language Derwent Abstract of EP 0 766 958, Jul. 1997.
English language Derwent Abstract of EP 0 795 313, Sep. 1997.
English language Derwent Abstract of FR 2 586 913, Mar. 1987.
English language Derwent Abstract of FR 2 733 749, Nov. 1996.
English language Derwent Abstract of JP 2019576, Jan. 1990.
English language Derwent Abstract of JP 9–110659, Apr. 1997.

* cited by examiner

COMPOSITION FOR THE OXIDATION DYEING OF KERATIN FIBRES AND DYEING PROCESS USING THIS COMPOSITION

The invention relates to a composition for the oxidation dyeing of keratin fibres, and in particular human keratin fibres such as the hair, comprising, in a medium which is suitable for dyeing, at least one first oxidation base chosen from paraphenylenediamine derivatives, double bases, orthoaminophenols and heterocyclic bases, at least one second oxidation base chosen from para-aminophenols, at least one meta-aminophenol as coupler and at least one enzyme of 2-electron oxidoreductase type in the presence of at least one donor for the said enzyme, and to the dyeing process using this composition.

It is known to dye keratin fibres, and in particular human hair, with dye compositions containing oxidation dye precursors, in particular ortho- or para-phenylenediamines, ortho- or para-aminophenols and heterocyclic bases, which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used as oxidation bases and couplers allows a wide range of colours to be obtained.

The so-called "permanent" coloration obtained by means of these oxidation dyes must moreover satisfy a certain number of requirements. Thus, it must have no toxicological drawbacks, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible colour differences along the same length of keratin fibre, which may in fact be differently sensitized (i.e. damaged) between its tip and its root.

The oxidation dyeing of keratin fibres is generally carried out in alkaline medium, in the presence of hydrogen peroxide. However, the use of alkaline media in the presence of hydrogen peroxide have the drawback of causing appreciable degradation of the fibres, as well as considerable bleaching of the keratin fibres, which is not always desirable.

The oxidation dyeing of keratin fibres can also be carried out using oxidizing systems other than hydrogen peroxide, such as enzymatic systems. Thus, it has already been proposed to dye keratin fibres, in particular in patent application EP-A-0,310,675, with compositions comprising an oxidation base and optionally a coupler, in combination with enzymes such as pyranose oxidase, glucose oxidase or uricase, in the presence of a donor for the said enzymes. Although being used under conditions which do not result in a degradation of the keratin fibres which is comparable to that caused by the dyes used in the presence of hydrogen peroxide, these dyeing processes nevertheless lead to colorations which are not entirely satisfactory, in particular as regards their intensity and resistance to the various attacking factors to which the hair may be subjected.

The Applicant has now discovered that it is possible to obtain new dyes, which are capable of leading to intense and chromatic colorations, without giving rise to any significant degradation of the keratin fibres, and which are relatively unselective and show good resistance to the various attacking factors to which the hair may be subjected, by combining at least one first oxidation base chosen from para-phenylenediamine derivatives other than para-phenylenediamine, double bases, ortho-aminophenols and heterocyclic bases, at least one second oxidation base chosen from para-aminophenols, at least one meta-aminophenol as coupler and at least one enzyme of 2-electron oxidoreductase type in the presence of at least one donor for the said enzyme.

This discovery forms the basis of the present invention.

A first subject of the invention is thus a ready-to-use composition for the oxidation dyeing of keratin fibres, and in particular human keratin fibres such as the hair, characterized in that it comprises, in a medium which is suitable for dyeing:

at least one first oxidation base chosen from para-phenylenediamine derivatives other than para-phenylenediamine, double bases, ortho-aminophenols and heterocyclic bases, at least one second oxidation base chosen from para-aminophenols, at least one meta-aminophenol as coupler, at least one enzyme of 2-electron oxidoreductase type, and at least one donor for the said enzyme.

The ready-to-use dye composition in accordance with the invention leads to intense relatively unselective colorations with excellent properties of resistance both to atmospheric agents such as light and bad weather and to perspiration and the various treatments to which the hair may be subjected (washing, permanent-waving).

A subject of the invention is also a process for the oxidation dyeing of keratin fibres using this ready-to-use dye composition.

The 2-electron oxidoreductase(s) used in the ready-to-use dye composition in accordance with the invention can be chosen in particular from pyranose oxidases, glucose oxidases, glycerol oxidases, lactate oxidases, pyruvate oxidases and uricases.

According to the invention, the 2-electron oxidoreductase is preferably chosen from uricases of animal, microbiological or biotechnological origin.

By way of example, mention may be made of uricase extracted from boar liver, uricase from *Arthrobacter globiformis*, as well as uricase from *Aspergillus flavus*.

The 2-electron oxidoreductase(s) can be used in pure crystalline form or in a form diluted in a diluent which is inert with respect to the said 2-electron oxidoreductase.

The 2-electron oxidoreductase(s) in accordance with the invention preferably represent(s) from 0.01 to 20% by weight approximately relative to the total weight of the ready-to-use dye composition, and even more preferably from 0.1 to 5% by weight approximately relative to this weight.

According to the invention, the term donor is understood to refer to the various substrates involved in the functioning of the said 2-electron oxidoreductase(s).

The nature of the donor (or substrate) for the said enzyme varies depending on the nature of the 2-electron oxidoreductase used. For example, as donors for the pyranose oxidases, mention may be made of D-glucose, L-sorbose and D-xylose; as a donor for the glucose oxidases, mention may be made of D-glucose; as donors for the glycerol oxidases, mention may be made of glycerol and dihydroxyacetone; as donors for the lactate oxidases, mention may be made of lactic acid and its salts; as donors for the pyruvate oxidases, mention may be made of pyruvic acid and its salts; and lastly, as donors for the uricases, mention may be made of uric acid and its salts.

The donor(s) (or substrate(s)) used in accordance with the invention preferably represent(s) from 0.01 to 20% by weight approximately relative to the total weight of the ready-to-use dye composition in accordance with the invention, and even more preferably from 0.1 to 5% by approximately relative to this weight.

Among the para-aminophenols which can be used as second oxidation base in the dye compositions according to the invention, mention may be made in particular of the compounds corresponding to formula (II) below, and the addition salts thereof with an acid:

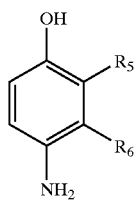
(II)

in which:

$R_5$ represents a hydrogen or halogen atom or a $C_1$–$C_4$ alkyl, $C_1$–$C_4$ monohydroxyalkyl, ($C_1$–$C_4$)alkoxy ($C_1$–$C_4$)alkyl, $C_1$–$C_4$ aminoalkyl or hydroxy($C_1$–$C_4$) alkylamino ($C_1$–$C_4$) alkyl radical, $R_6$ represents a hydrogen or halogen atom or a $C_1$–$C_4$ alkyl, $C_1$–$C_4$ monohydroxyalkyl, $C_2$–$C_4$ polyhydroxyalkyl, $C_1$–$C_4$ aminoalkyl, cyano ($C_1$–$C_4$) alkyl or ($C_1$–$C_4$) alkoxy($C_1$–$C_4$) alkyl radical, it being understood that at least one of the radicals $R_5$ or $R_6$ represents a hydrogen atom.

Among the para-aminophenols of formula (II) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino -2-aminomethylphenol, 4-amino-2-(β-hydroxyethylaminomethyl)phenol and 4-amino-2-fluorophenol, and the addition salts thereof with an acid.

The para-aminophenol(s) which can be used as second oxidation base preferably represent(s) from 0.0005 to 12% by weight approximately relative to the total weight of the ready-to-use dye composition in accordance with the invention, and even more preferably from 0.005 to 6% by weight approximately relative to this weight.

The meta-aminophenol(s) which can be used as coupler in the ready-to-use dye composition in accordance with the invention is (are) preferably chosen from the compounds of formula (III) below, and the addition salts thereof with an acid:

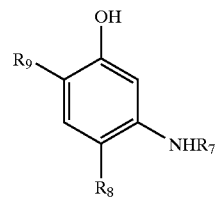
(III)

in which:

$R_7$ represents a hydrogen atom or a $C_1$–$C_4$ alkyl, $C_1$–$C_4$ monohydroxyalkyl or $C_2$–$C_4$ polyhydroxyalkyl radical, $R_8$ represents a hydrogen atom, a $C_1$–$C_4$ alkyl or $C_1$–$C_4$ alkoxy radical or a halogen atom chosen from chlorine, bromine and fluorine, $R_9$ represents a hydrogen atom or a $C_1$–$C_4$ alkyl, $C_1$–$C_4$ alkoxy, $C_1$–$C_4$ monohydroxyalkyl, $C_2$–$C_4$ polyhydroxyalkyl, $C_1$–$C_4$ monohydroxyalkoxy or $C_2$–$C_4$ polyhydroxyalkoxy radical.

Among the meta-aminophenols of formula (III) above, mention may be made more particularly of meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol and 5-(γ-hydroxypropylamino)-2-methylphenol, and the addition salts thereof with an acid.

The meta-aminophenol(s) which can be used as coupler preferably represent(s) from 0.0001 to 8% by weight approximately relative to the total weight of the ready-to-use dye composition, and even more preferably from 0.005 to 5% by weight approximately relative to this weight.

Among the para-phenylenediamine derivatives which can be used as first oxidation base in the ready-to-use dye composition in accordance with the invention, mention may be made in particular of the compounds of formula (I) below, and the addition salts thereof with an acid:

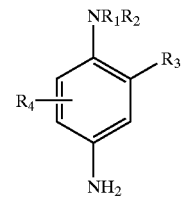
(I)

in which:

$R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical, a $C_1$–$C_4$ alkyl radical substituted with a nitrogenous group, a phenyl radical or a 4'-aminophenyl radical;

$R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted with a nitrogenous group;

$R_3$ represents a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino($C_1$–$C_4$)-alkoxy radical, a $C_1$–$C_4$ mesylaminoalkoxy radical or a carbamoylamino ($C_1$–$C_4$) alkoxy radical, $R_4$ represents a hydrogen or halogen atom or a $C_1$–$C_4$ alkyl radical;

it being understood that at least one of the radicals $R_1$ to $R_4$ is other than a hydrogen atom.

Among the nitrogenous groups of formula (I) above, mention may be made in particular of amino, mono ($C_1$–$C_4$) alkylamino, di($C_1$–$C_4$) alkylamino, tri($C_1$–$C_4$)-alkylamino, monohydroxy($C_1$–$C_4$)alkylamino, imidazolinium and ammonium radicals.

Among the para-phenylenediamine derivatives of formula (I) above, mention may be made more particularly of para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl) aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylene-diamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamine derivatives of formula (I) above, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the addition salts thereof with an acid are most particularly preferred.

According to the invention, the term double bases is understood to refer to the compounds containing at least two aromatic rings bearing amino and/or hydroxyl groups.

Among the double bases which can be used as first oxidation base in the ready-to-use dye composition in accordance with the invention, mention may be made in particular of the compounds of formula (IV) below, and the addition salts thereof with an acid:

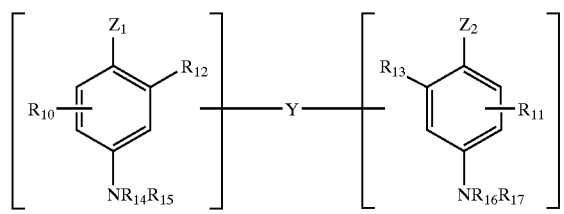

(IV)

in which:

$Z_1$ and $Z_2$, which may be identical or different, represent a hydroxyl or —$NH_2$ radical which may be substituted with a $C_1$–$C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1$–$C_6$ alkoxy radicals;

$R_{10}$ and $R_{11}$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;

$R_{12}$, $R_{13}$, $R_{14}$, $R_{15}$, $R_{16}$ and $R_{17}$, which may be identical or different, represent a hydrogen atom, a linker arm Y or a $C_1$–$C_4$ alkyl radical; it being understood that the compounds of formula (IV) contain only one linker arm Y per molecule.

Among the nitrogenous groups of formula (IV) above, mention may be made in particular of amino, mono ($C_1$–$C_4$) alkylamino, di($C_1$–$C_4$)alkylamino, tri($C_1$–$C_4$)-alkylamino, monohydroxy($C_1$–$C_4$)alkylamino, imidazolinium and ammonium radicals.

Among the double bases of formula (IV) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)-ethylenediamine and 1,8-bis(2,5-diaminophenoxy)-3,5-dioxaoctane, and the addition salts thereof with an acid.

Among these double bases of formula (IV), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

Among the ortho-aminophenols which can be used as first oxidation base in the ready-to-use dye composition in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as first oxidation base in the dye composition in accordance with the invention, mention may be made more particularly of pyridine derivatives, pyrimidine derivatives, pyrazole derivatives and pyrazolo-pyrimidine derivatives, and the addition salts thereof with an acid.

Among the pyridine derivatives, mention may be made more particularly of the compounds described, for example, in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-10659 or patent applications WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof with an acid.

Among the pyrazole derivatives, mention may be made more particularly of the compounds described in patents DE 3,843,892, DE 4,133,957 and patent applications WO 94/08969, WO 94/08970, FR-A-2,733,749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Among the pyrazolopyrimidine derivatives, mention may be made more particularly of the pyrazolo[1,5-a]pyrimidines of formula (V) below, and the addition salts thereof with an acid or with a base and the tautomeric forms thereof, when a tautomeric equilibrium exists:

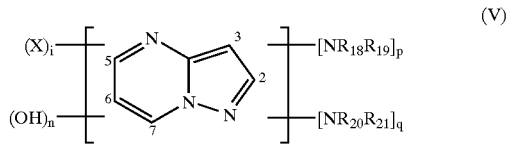

(V)

in which:
- $R_{18}$, $R_{19}$, $R_{20}$ and $R_{21}$, which may be identical or different, denote a hydrogen atom, a $C_1$–$C_4$ alkyl radical, an aryl radial, a $C_1$–$C_4$ hydroxyalkyl radical, a $C_2$–$C_4$ polyhydroxyalkyl radical, a ($C_1$–$C_4$)alkoxy($C_1$–$C_4$)alkyl radical, a $C_1$–$C_4$ aminoalkyl radical (it being possible for the amine to be protected with an acetyl, ureido or sulphonyl radical), a ($C_1$–$C_4$)alkylamino($C_1$–$C_4$ radical, a di[($C_1$–$C_4$)alkyl]amino($C_1$–$C_4$)alkyl radical (it being possible for the dialkyl radicals to form a 5- or 6-membered carbon-based ring or a heterocycle), a hydroxy($C_1$–$C_4$) alkyl- or di[hydroxy($C_1$–$C_4$) alkyl] amino($C_1$–$C_4$) alkyl radical;
- the radicals X, which may be identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a ($C_1$–$C_4$) alkylamino ($C_1$–$C_4$) alkyl radical, a di[($C_1$–$C_4$)alkyl] amino($C_1$–$C_4$)alkyl radical (it being possible for the dialkyls to form a 5- or 6-membered carbon-based ring or a heterocycle), a hydroxy($C_1$–$C_4$)alkyl- or di-[hydroxy($C_1$–$C_4$)alkyl]amino($C_1$–$C_4$)alkyl radical, an amino radical, a ($C_1$–$C_4$)alkyl- or di[($C_1$–$C_4$)alkyl] amino radical; a halogen atom, a carboxylic acid group, a sulphonic acid group;
- i is equal to 0, 1, 2 or 3;
- p is equal to 0 or 1;
- q is equal to 0 or 1;
- n is equal to 0 or 1;
with the proviso that:
  the sum p+q is other than 0;
  when p+q is equal to 2, then n is equal to 0 and the groups $NR_{18}R_{19}$ and $NR_{20}R_{21}$ occupy the (2,3); (5,6); (6,7); (3,5) or (3,7) positions;

when p+q is equal to 1, then n is equal to 1 and the group $NR_{18}R_{19}$ (or $NR_{20}R_{21}$) and the OH group occupy the (2,3); (5,6); (6,7); (3,5) or (3,7) positions.

When the pyrazolo[1,5-a]pyrimidines of formula (V) above are such that they contain a hydroxyl group on one of the positions 2, 5 or 7 α to a nitrogen atom, a tautomeric equilibrium exists represented, for example, by the following scheme:

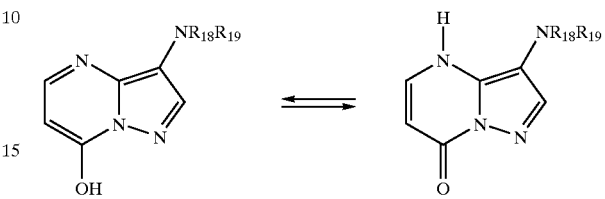

Among the pyrazolo[1,5-a]pyrimidines of formula (V) above, mention may be made in particular of:
- pyrazolo[1,5-a]pyrimidine-3,7-diamine;
- 2,5-dimethylpyrazolo[1,5-a]pyrimidine-3,7-diamine;
- pyrazolo[1,5-a]pyrimidine-3,5-diamine;
- 2,7-dimethylpyrazolo[1,5-a]pyrimidine-3,5-diamine;
- 3-aminopyrazolo[1,5-a]pyrimidin-7-ol;
- 3-aminopyrazolo[1,5-a]pyrimidin-5-ol;
- 2-(3-aminopyrazolo[1,5-a]pyrimidin-7-ylamino)ethanol;
- 2-(7-aminopyrazolo[1,5-a]pyrimidin-3-ylamino)ethanol;
- 2-[(3-aminopyrazolo[1,5-a]pyrimidin-7-yl)-(2-hydroxyethyl)amino]ethanol;
- 2-[(7-aminopyrazolo[1,5-a]pyrimidin-3-yl)-(2-hydroxyethyl)amino]ethanol;
- 5,6-dimethylpyrazolo[1,5-a]pyrimidine-3,7-diamine;
- 2,6-dimethylpyrazolo[1,5-a]pyrimidine-3,7-diamine;
- 2,5, N7, N7-tetramethylpyrazolo[1,5-a]pyrimidine-3,7-diamine;

and the addition salts thereof and the tautomeric forms thereof, when a tautomeric equilibrium exists.

The pyrazolo[1-5-a]pyrimidines of formula (V) above can be prepared by cyclization starting with an aminopyrazole, according to the syntheses described in the following references:

EP 628559 Beiersdorf-Lilly.
R. Vishdu, H. Navedul, Indian J. Chem., 34b (6), 514, 1995.
N. S. Ibrahim, K. U. Sadek, F. A. Abdel-Al, Arch. Pharm., 320, 240, 1987.
R. H. Springer, M. B. Scholten, D. E. O'Brien, T. Novinson, J. P. Miller, R. K. Robins, J. Med. Chem., 25, 235, 1982.
T. Novinson, R. K. Robins, T. R. Matthews, J. Med. Chem., 20, 296, 1977.
U.S. Pat. No. 3,907,799 ICN Pharmaceuticals.

The pyrazolo[1-5-a]pyrimidines of formula (V) above can also be prepared by cyclization starting from hydrazine, according to the syntheses described in the following references:

A. McKillop and R. J. Kobilecki, Heterocycles, 6(9), 1355, 1977.
E. Alcade, J. De Mendoza, J. M. Marcia-Marquina, C. Almera, J. Elguero, J. Heterocyclic Chem., 11(3), 423, 1974.
K. Saito, I. Hori, M. Higarashi, H. Midorikawa, Bull. Chem. Soc. Japan, 47(2), 476, 1974.

The para-phenylenediamine derivative(s) and/or the double base(s) and/or the ortho-aminophenol(s) and/or the heterocyclic base(s) which can be used as first oxidation base preferably represent(s) from 0.0005 to 12% by weight approximately relative to the total weight of the ready-to-use dye composition according to the invention, and even more preferably from 0.005 to 6% by weight approximately relative to this weight.

The ready-to-use dye composition in accordance with the invention can also contain one or more additional couplers other than meta-aminophenols used according to the invention and/or one or more direct dyes, in particular in order to modify the shades or to enrich them with glints.

Among the couplers which can be present additionally in the ready-to-use dye composition in accordance with the invention, mention may be made in particular of meta-phenylenediamines, meta-diphenols and heterocyclic couplers, and the addition salts thereof with an acid.

When they are present, these additional couplers preferably represent from 0.0001 to 10% by weight approximately relative to the total weight of the ready-to-use dye composition, and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for dyeing (or support) for the ready-to-use dye composition in accordance with the invention generally consists of water or a mixture of water and at least one organic solvent to dissolve the compounds which would not be sufficiently soluble in water. By way of organic solvents, mention may be made, for example, of $C_1$–$C_4$ alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the ready-to-use dye composition, and even more preferably between 5 and 30% by weight approximately.

The pH of the ready-to-use composition in accordance with the invention is chosen such that the enzymatic activity of the 2-electron oxidoreductase is sufficient. It is generally between 5 and 11 approximately, and preferably between 6.5 and 10 approximately. It can be adjusted to the desired value using acidifying or basifying agents usually used for dyeing keratin fibres.

Among the acidifying agents, mention may be made, by way of example, of inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, mention may be made, by way of example, of aqueous ammonia, alkaline carbonates, alkanolamines such as mono-, di- and triethanolamines, 2-methyl-2-aminopropanol and derivatives thereof, sodium hydroxide, potassium hydroxide and the compounds of formula (VI) below:

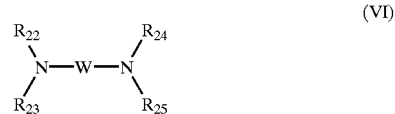

(VI)

in which W is a propylene residue optionally substituted with a hydroxyl group or a $C_1$–$C_4$ alkyl radical; $R_{22}$, $R_{23}$, $R_{24}$ and $R_{25}$, which may be identical or different, represent a hydrogen atom or a $C_1$–$C_4$ alkyl or $C_1$–$C_4$ hydroxyalkyl radical.

The ready-to-use dye composition in accordance with the invention can also contain various adjuvants used conventionally in compositions for the dyeing of the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, enzymes other than the 2-electron oxidoreductases used in accordance with the invention, such as, for example, peroxidases, penetration agents, sequestering agents, fragrances, buffers, dispersing agents, conditioners such as, for example, silicones which may or may not be volatile or modified, film-forming agents, ceramides, preserving agents and opacifiers.

Needless to say, a person skilled in the art will take care to select this or these optional complementary compound(s) such that the advantageous properties intrinsically associated with the ready-to-use dye composition in accordance with the invention are not, or are not substantially, adversely affected by the addition or additions envisaged.

The ready-to-use dye composition in accordance with the invention can be in various forms, such as in the form of liquids, creams or gels, which may be pressurized, or in any other form which is suitable for dyeing keratin fibres, and in particular human hair. In this case the oxidation dyes and the 2-electron oxidoreductase(s) are present in the same ready-to-use composition, and consequently the said composition must be free of gaseous oxygen, so as to avoid any premature oxidation of the oxidation dye(s).

A subject of the invention is also a process for dyeing keratin fibres, and in particular human keratin fibres such as the hair, using the ready-to-use dye composition as defined above.

According to this process, at least one ready-to-use dye composition as defined above is applied to the fibres, for a period which is sufficient to develop the desired coloration, after which the fibres are rinsed, optionally washed with shampoo, rinsed again and dried.

The time required to develop the coloration on the keratin fibres is usually between 3 and 60 minutes and even more precisely between 5 and 40 minutes.

According to one specific embodiment of the invention, the process includes a preliminary step which consists in separately storing, on the one hand, a composition (A) comprising, in a medium which is suitable for dyeing, at least one first oxidation base chosen from para-phenylenediamine derivatives, double bases, ortho-aminopehnols and heterocyclic bases, at least one second oxidation base chosen from para-aminophenols, at least one meta-aminophenol as coupler, and, on the other hand, a composition (B) comprising, in a medium which is suitable for dyeing, at least one enzyme of 2-electron oxidoreductase type in the presence of at least one donor for the said enzyme, and then in mixing them together at the time of use, after which this mixture is applied to the keratin fibres.

Another subject of the invention is a multi-compartment dyeing device or "kit" or any other multi-compartment packaging system, a first compartment of which comprises composition (A) as defined above and a second compartment of which comprises composition (B) as defined above. These devices can be equipped with means for delivering the desired mixture onto the hair, such as the devices described in patent FR-2,586,913 in the name of the Applicant.

The examples which follow are intended to illustrate the invention without, however, limiting its scope.

EXAMPLES

DYEING EXAMPLES 1 and 2

The ready-to-use dye compositions below were prepared (contents in grams):

| COMPOSITION | 1 | 2 |
|---|---|---|
| 2-β-Hydroxyethyl-para-phenylenediamine dihydrochloride (oxidation base) | 0.45 | 0.45 |
| para-Aminophenol (oxidation base) | 0.1 | 0.1 |
| meta-Aminophenol (coupler) | 0.1 | — |
| 2-Methyl-5-aminophenol (coupler) | — | 0.13 |
| Uricase from Arthrobacter globiformis, at 20 international units (I.U.)/mg, sold by the company Sigma | 1.5 | 1.5 |
| Uric acid | 1.5 | 1.5 |
| Common dye support (*) | (*) | (*) |
| Demineralized water qs | 100 g | 100 g |

| (*): Common dye support: | |
|---|---|
| Ethanol | 20.0 g |
| Hydroxyethylcellulose sold under the name Natrosol 250 HR ® by the company Aqualon | 1.0 g |
| Poly ($C_8$–$C_{10}$) alkylglucoside as an aqueous solution containing 60% active material (A.M.) buffered with ammonium citrate (0.5%), sold under the name Oramix CG110 ® by the company SEPPIC | 8.0 g |
| Monoethanolamine qs | pH = 9.5 |

Each of the ready-to-use dye compositions described above was applied to locks of natural grey hair containing 90% white hairs, for 30 minutes. The hair was then rinsed, washed with a standard shampoo and then dried.

The hair was dyed in the shades given in the table below:

| EXAMPLE | Shade obtained |
|---|---|
| 1 | Dark pearlescent blonde |
| 2 | Dark mahogany blonde |

What is claimed is:

1. A ready-to-use composition for the oxidation dyeing of keratin fibers, comprising:

at least one first oxidation base chosen from para-phenylenediamine compounds chosen from: 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof, double bases chosen from: N,N'-bis(β-hydroxyethyl)-N,N'-bis(4'-aminophenyl)-1,3-diaminopropanol, N,N'-bis(β-hydroxyethyl)-N,N'-bis(4-'-amino-phenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and acid-addition salts thereof, ortho-aminophenols chosen from: 2-amino-5-methylphenol, 2-amino-6-methylphenol, 5-acetamido-2-aminophenol, and acid-addition salts thereof, pyridine compounds chosen from: 2,5-diaminopyridine, 2-(4-methoxyphenyl)amino-3-amino-pyridine, 2,3-diamino-6-methoxypyridine, 2-(β-methoxy-ethyl) amino-3-amino-6-methoxypyridine, 3,4-diaminopyridine, and acid-addition salts thereof, pyrimidine compounds chosen from: 2,4,5,6-tetraamino-pyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-tri-amino-pyrimidine, and acid-addition salts thereof, pyrazole compounds chosen from: 4,5-diamino-1-methyl-pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-di-methyl-5-hydrazinopyrazole, 1-benzyl-4,5-diamino-3-methyl-pyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-iso-propyl-pyrazole, 4,5-diamino-3-methyl-1-isopropyl-pyrazole, 4-amino-5-(2'-amino-ethyl)amino-1,3-dimethyl-pyrazole, 3,4,5-triamino-pyrazole, 1-methyl-3,4,5-tri-amino-pyrazole, 3,5-diamino-1-methyl-4-methylamino-pyrazole, 3,5-diamino-4-(β-hydroxyethyl)amino-1-methyl-pyrazole, and acid-addition salts thereof, pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino) ethanol;
2-(7-aminopyrazolo[1,5-a]pyrimidin-3-ylamino) ethanol;

2-[(3-aminopyrazolo[1,5-a]pyrimidin-7-yl)-(2-hydroxy-ethyl)amino]ethanol;
2-[(7-aminopyrazolo[1,5-a]pyrimidin-3-yl)-(2-hydroxy-ethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
and addition salts thereof and the tautomeric forms thereof, when a tautomeric equilibrium exists;

at least one second oxidation base chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, 4-amino-2-fluorophenol, and acid-addition salts thereof;

at least one meta-aminophenol coupler chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenyl, 5-N-(β-hydroxyethyl)amino-4-methoxy-2-methylphenyl, 5-amino-4-methoxy-2-methylphenyl, 5-amino-4-chloro-2-methylphenol, 5-amino-2,4-dimethoxyphenol, 5-(γ-hydroxypropylamino)-2-methylphenol and acid-addition salts thereof;

at least one 2-electron oxidoreductase chosen from pyranose oxidases, glucose oxidases, glycerol oxidases, lactate oxidases, pyruvate oxidases and uricases; and at least one donor for said 2-electron oxidoreductase chosen from D-glucose, L-sorbose, D-xylose, glycerol, dihydroxyacetone, lactic acid and salts thereof; pyruvic acid and salts thereof; and uric acid and salts thereof.

2. A process for dyeing keratin fibers, comprising applying at least one ready-to-use dye composition for the oxidation dyeing of keratin fibers to said fibers and developing for a period sufficient to achieve the desired coloration, wherein said ready-to-use dye composition comprises:

at least one first oxidation base chosen from para-phenylenediamine compounds chosen from: 2,3-dimethyl-para-phenylene-diamine, 2,6-dimethyl-para-phenylenediamine, 2,6-diethyl-para-phenylene-diamine, 2,5-dimethyl-para-phenylenediamine, N,N-dimethyl-para-phenylenediamine, N,N-diethyl-para-phenylenediamine, N,N-dipropyl-para-phenylene-diamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof,
double bases chosen from: N,N'-bis(β-hydroxyethyl)-N,N'-bis(4'-aminophenyl)-3-diaminopropanol, N,N'-bis(β-hydroxyethyl)-N,N'-bis(4'-amino-phenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and acid-addition salts thereof, ortho-aminophenols chosen from: 2-amino-5-methylphenol, 2-amino-6-methylphenol, 5-acetamido-2-aminophenol, and acid-addition salts thereof, pyridine compounds chosen from: 2,5-diaminopyridine, 2-(4-methoxyphenyl)amino-3-amino-pyridine, 2,3-diamino-6-methoxypyridine, 2-(β-methoxy-ethyl) amino-3-amino-6-methoxypyridine, 3,4-diaminopyridine, and acid-addition salts thereof, pyrimidine compounds chosen from: 2,4,5,6-tetraamino-pyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-tri-amino-pyrimidine, and acid-addition salts thereof, pyrazole compounds chosen from: 4,5-diamino-1-methyl-pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-di-methyl-5-hydrazinopyrazole, 1-benzyl-4,5-diamino-3-methyl-pyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-iso-propyl-pyrazole, 4,5-diamino-3-methyl-1-isopropyl-pyrazole, 4-amino-5-(2'-amino-ethyl)amino-1,3-dimethyl-pyrazole, 3,4,5-triamino-pyrazole, 1-methyl-3,4,5-tri-amino-pyrazole, 3,5-diamino-1-methyl-4-methylamino-pyrazole, 3,5-diamino-4-(β-hydroxyethyl)amino-1-methyl-pyrazole, and acid-addition salts thereof, pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino) ethanol;
2-(7-aminopyrazolo[1,5-a]pyrimidin-3-ylamino) ethanol;
2-[(3-aminopyrazolo[1,5-a]pyrimidin-7-yl)-(2-hydroxy-ethyl)amino]ethanol;
2-[(7-aminopyrazolo[1,5-a]pyrimidin-3-yl)-(2-hydroxy-ethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
and addition salts thereof and the tautomeric forms thereof, when a tautomeric equilibrium exists;

at least one second oxidation base chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof;

at least one meta-aminophenol coupler chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol 5-(γ-hydroxypropylamino)-2-methylphenol, and acid-addition salts thereof;

at least one 2-electron oxidoreductase chosen from pyranose oxidases, glucose oxidases, glycerol oxidases, lactate oxidases, pyruvate oxidases and uricases;

at least one donor for said 2-electron oxidoreductase chosen from D-glucose, L-sorbose, D-xylose, glycerol, dihydroxyacetone, lactic acid and salts thereof; pyruvic acid and salts thereof; and uric acid and salts thereof.

3. A ready-to-use composition for the oxidation dyeing of keratin fibers, comprising:

at least one first oxidation base chosen from:

para-phenylenediamine compounds chosen from: 2,3-dimethyl:para-phenylenediamine, 2,6-dimethyl-para-phenylenediamine, 2,6-diethyl=para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2,βhydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, 3N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-par -phenylenediamine, N-(β-methoxyethyl)-para-phenylenediamine, and acid-addition salts thereof, double bases chosen from: N,N'-bis-(β-hydroxyethyl)-N,N'-bis(4'-amino-phenyl)-1,3-diaminopropanol, N,N'-bis(β-hydroxyethyl)-N,N'-bis(4'-aminophenyl)ethylenediamine, N,N'-bis-(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine N,N'-bis-(ethyl )-N,N'-bis(4'-amino-3'-methylphenyl)ethylenediamine, 1,8-bis(2,5-diaminophenoxy)-3,5-dioxaoctane, and acid-addition salts thereof, ortho-aminophenols chosen from: 2-amino-5-methylphenol, 2-amino-6-methylphenol, 5-acetamido-2-aminophenol, and acid-addition salts thereof, pyridine compounds;

pyrimidine compounds;

pyrazole compounds; and pyrazolopyrimidine compounds;

and addition salts thereof and the tautomeric forms thereof, when a tautomeric equilibrium exists;

at least one second oxidation base chosen from para-aminophenols and acid-addition salts thereof;

at least one coupler chosen from meta-aminophenols and acid-addition salts thereof;

at least one enzyme chosen from 2-electron oxidoreductases, and at least one donor for said at least one enzyme.

4. A ready-to-use composition according to claim 3, wherein said at least one 2-electron oxidoreductase is chosen from pyranose oxidases, glucose oxidases, glycerol oxidases, lactate oxidases, pyruvate oxidases and uricases.

5. A ready-to-use composition according to claim 3, wherein said at least one 2-electron oxidoreductase is chosen from uricases of animal, microbiological and biotechnological origin.

6. A ready-to-use composition according to claim 3, wherein said at least one 2-electron oxidoreductase is present in an amount ranging from 0.01 to 20% by weight relative to the total weight of the composition.

7. A ready-to-use composition according to claim 6, wherein said at least one 2-electron oxidoreductase is present in an amount ranging from 0.1 to 5% by weight relative to the total weight of the composition.

8. A ready-to-use composition according to claim 3, wherein said at least one donor for said at least one 2-electron oxidoreductase is chosen from D-glucose, L-sorbose, D-xylose, glycerol, dihydroxyacetone, lactic acid and its salts, pyruvic acid and its salts, and uric acid and its salts.

9. A ready-to-use composition according to claim 8, wherein said at least one donor for said at least one 2-electron oxidoreductase is chosen from uric acid and its salts.

10. A ready-to-use composition according to claim 3, wherein said at least one donor is present in an amount ranging from 0.01 to 20% by weight relative to the total weight of the composition.

11. A ready-to-use composition according to claim 10, wherein said at least one donor is present in an amount ranging from 0.1 to 5% by weight relative to the total weight of the composition.

12. A ready-to-use composition according to claim 3, wherein said at least one second oxidation base is present in an amount ranging from 0.0005 to 12% by weight relative to the total weight of the composition.

13. A ready-to-use composition according to claim 12, wherein said at least one second oxidation base is present in an amount ranging from 0.005 to 6% by weight relative to the total weight of the composition.

14. A ready-to-use composition according to claim 3, wherein said at least one coupler is chosen from meta-amino phenols of formula (III) below, and acid-addition salts thereof:

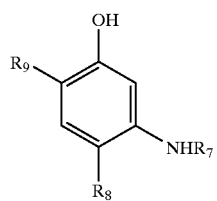

(III)

in which:

R₇ is chosen from a hydrogen atom, $C_1$–$C_4$ alkyl radicals, $C_1$–$C_4$ monohydroxyalkyl radicals and $C_2$–$C_4$ polyhydroxyalkyl radicals, R₈ is chosen from a hydrogen atom, $C_1$–$C_4$ alkyl radicals, $C_1$–$C_4$ alkoxy radicals and halogen atoms, R₉ is chosen from a hydrogen atom, $C_1$–$C_4$ alkyl radicals, $C_1$–$C_4$ alkoxy radicals, $C_1$–$C_4$ monohydroxyalkyl radicals, $C_2$–$C_4$ polyhydroxyalkyl radicals, $C_1$–$C_4$ monohydroxyalkoxy radicals, and $C_2$–$C_4$ polyhydroxyalkoxy radicals.

15. A ready-to-use composition according to claim 14, wherein said at least one coupler of formula (III) is chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol and acid-addition salts thereof.

16. A ready-to-use composition according to claim 3, wherein said at least one coupler is present in an amount ranging from 0.0001 to 8% by weight relative to the total weight of the composition.

17. A ready-to-use composition according to claim 16, wherein said at least one coupler is present in an amount ranging from 0.005 to 5% by weight relative to the total weight of the composition.

18. A ready-to-use composition according to claim 3, wherein said at least one first oxidation base is present in an amount ranging from 0.0005 to 12% by weight relative to the total weight of the composition.

19. A ready-to-use composition according to claim 18, wherein said at least one first oxidation base is present in an amount ranging from 0.005 to 6% by weight relative to the total weight of the composition.

20. A ready-to-use composition according to claim 3, wherein said acid-addition salts are chosen from hydrochlorides, hydrobromides, sulphates, tartrates, lactates and acetates.

21. A ready-to-use composition according to claim 3, wherein said composition further comprises water or a mixture of water and at least one organic solvent.

22. A ready-to-use composition according to claim 3, wherein said composition has a pH ranging from 5 to 11.

23. A ready-to-use composition according to claim 3, further comprising at least one peroxidase.

* * * * *

UNITED STATES PATENT AND TRADEMARK OFFICE
CERTIFICATE OF CORRECTION

PATENT NO. : 6,783,559 B2
DATED : August 31, 2004
INVENTOR(S) : Roland De La Mettrie et al.

It is certified that error appears in the above-identified patent and that said Letters Patent is hereby corrected as shown below:

Column 13,
Line 22, "5-N-(β-hydroxyethyl)amino-2-methylphenyl," should read
-- 5-N-(β-hydroxyethyl)amino-2-methylphenol, --.
Lines 22-23, "5-N-(β-hydroxyethyl)amino-4-methoxy-2-methylphenyl," should read
-- 5-N-(β-hydroxyethyl)amino-4-methoxy-2-methylphenol, --.
Line 24, "5-amino-4-methoxy-2-methylphenyl," should read
-- 5-amino-4-methoxy-2-methoxy-2-methylphenol, --.
Lines 65-66, "N,N'-bis(β-hydroxyethyl)-N,N'-bis(4'-aminophenyl)-3-diaminopropanol," should read -- N,N'-bis(β-hydroxyethyl)-N,N'-bis(4'-aminophenyl)-1,3-diaminopropanol, --.

Column 15,
Lines 24-25, "2,3-dimethyl:para-phenylenediamine," should read -- 2,3-dimethyl-para-phenylenediamine, --.
Lines 26-27, "2,6-diethyl=para-phenylenediamine," should read
-- 2,6-diethyl-para-phenylenediamine, --.
Line 34, "2,βhydroxyethyl-para-phenylenediamine," should read
-- 2,β-hydroxyethyl-para-phenylenediamine, --.
Lines 39-40, "3N,N-(ethyl-β-hydroxyethyl)-para-phenylenediamine," should read
-- N,N-(ethyl-β-hydroxyethyl)-para-phenylenediamine, --.
Lines 43-44, "2-β-acetylaminoethyloxy-par -phenylenediamine," should read
-- 2-β-acetylaminoethyloxy-para-phenylenediamine, --.
Lines 53-54, after "N,N'-bis(4-methylaminophenyl)tetramethylenediamine", insert a comma.

Signed and Sealed this

Fourteenth Day of December, 2004

JON W. DUDAS
*Director of the United States Patent and Trademark Office*